United States Patent
Ornelas-Cravioto et al.

(10) Patent No.: US 7,351,424 B2
(45) Date of Patent: Apr. 1, 2008

(54) ENHANCED PURITY TRANS-LUTEIN-ESTER COMPOSITIONS AND METHODS OF MAKING SAME

(75) Inventors: Alejandro Ornelas-Cravioto, Guananjuato (MX); Enrique Hernandez-Hernandez, Queretaro (MX)

(73) Assignee: Bio Lut S.A. de C.V., San Antonio, TX (US)

( * ) Notice: Subject to any disclaimer, the term of this patent is extended or adjusted under 35 U.S.C. 154(b) by 252 days.

(21) Appl. No.: 10/986,049

(22) Filed: Nov. 12, 2004

(65) Prior Publication Data

US 2006/0020030 A1    Jan. 26, 2006

Related U.S. Application Data

(60) Provisional application No. 60/589,799, filed on Jul. 22, 2004.

(51) Int. Cl.
*A61K 47/00* (2006.01)

(52) U.S. Cl. ............... 424/439; 514/548; 514/552; 554/230

(58) Field of Classification Search ......... 568/18; 554/12, 230; 424/439; 514/548, 552
See application file for complete search history.

(56) References Cited

U.S. PATENT DOCUMENTS

| | | | |
|---|---|---|---|
| 2,527,602 A | 10/1950 | Wall | |
| 3,206,316 A | 9/1965 | Kläui | |
| 3,258,467 A | 6/1966 | Anderson et al. | |
| 3,333,962 A | 8/1967 | Prebluda et al. | |
| 3,523,138 A | 8/1970 | Grant | |
| 3,539,686 A | 11/1970 | Rosenberg | |
| 3,558,712 A | 1/1971 | Surmatis et al. | |
| 3,661,997 A | 5/1972 | Surmatis et al. | |
| 3,732,214 A | 5/1973 | Surmatis et al. | |
| 3,879,424 A | 4/1975 | Surmatis et al. | |
| 3,989,757 A | 11/1976 | Surmatis | |
| 3,997,679 A | 12/1976 | Salkin | |
| 4,028,217 A | 6/1977 | Okada et al. | |
| 4,048,203 A * | 9/1977 | Philip | 554/208 |
| 4,105,855 A | 8/1978 | Schulz et al. | |
| 4,316,917 A | 2/1982 | Antoshkiw et al. | |
| 4,851,339 A | 7/1989 | Hills | |
| 4,871,551 A | 10/1989 | Spencer | |
| 4,929,774 A | 5/1990 | Fukamachi et al. | |
| 5,019,668 A | 5/1991 | Keat et al. | |
| 5,157,132 A | 10/1992 | Tan et al. | |
| 5,180,747 A | 1/1993 | Matsuda et al. | |
| 5,290,605 A | 3/1994 | Shapira | |
| 5,382,714 A | 1/1995 | Khachik | |
| 5,523,494 A | 6/1996 | Torres-Cardona et al. | |
| 5,536,504 A | 7/1996 | Eugster et al. | |
| 5,602,286 A | 2/1997 | Muralidhara | |
| 5,607,707 A | 3/1997 | Ford et al. | |
| 5,643,623 A | 7/1997 | Schmitz et al. | |
| 5,648,564 A | 7/1997 | Ausich et al. | |
| 5,705,180 A | 1/1998 | Schlipalius | |
| 5,712,311 A | 1/1998 | Soudant et al. | |
| 5,747,544 A | 5/1998 | Garnett et al. | |
| 5,773,026 A | 6/1998 | Schlipalius | |
| 5,780,693 A | 7/1998 | Bernhard et al. | |
| 5,804,168 A | 9/1998 | Murad | |
| 5,834,044 A | 11/1998 | Schmitz et al. | |
| 5,847,238 A | 12/1998 | Muralidhara et al. | |
| 5,863,953 A | 1/1999 | Lüddecke et al. | |
| 5,871,766 A | 2/1999 | Hennekens | |
| 5,876,782 A | 3/1999 | Sas et al. | |
| 5,886,053 A | 3/1999 | Schmutzler et al. | |
| 5,891,907 A | 4/1999 | Kolter et al. | |
| 5,895,652 A | 4/1999 | Giampapa | |
| 5,895,659 A | 4/1999 | Lüddecke et al. | |
| 6,191,293 B1 * | 2/2001 | Levy | 554/12 |
| 6,221,417 B1 | 4/2001 | Sas et al. | |
| 6,262,284 B1 | 7/2001 | Khachik | |
| 6,313,169 B1 | 11/2001 | Bowen et al. | |
| 6,329,557 B1 | 12/2001 | Rodriguez et al. | |
| 6,380,442 B1 | 4/2002 | Madhavi et al. | |
| 6,660,297 B2 | 12/2003 | Bartels et al. | |
| 6,686,340 B2 | 2/2004 | Rath | |
| 6,716,451 B1 | 4/2004 | Udell et al. | |
| 6,737,535 B2 * | 5/2004 | Kumar | 554/21 |
| 6,743,953 B2 | 6/2004 | Kumar et al. | |
| 6,787,147 B1 | 9/2004 | Huner et al. | |

(Continued)

FOREIGN PATENT DOCUMENTS

DE    1 224 597    7/1962

(Continued)

OTHER PUBLICATIONS

Abstract of JP06-048895, Feb. 22, 1994, Japanese Patent Office.
Important facts about Xangold (natural lutein esters), Jun. 2003.
G.K. Gregory, et al., "Quantitative Analysis of Lutein Esters in Marigold Flowers (Tagetes erecta) by High Performance Liquid Chromatography", Journal of Food Science, vol. 51, No. 4, pp. 1093-1094.
"Xantopina Plus", Bioquimex Nutrition.
The FASEB Journal, Abstracts, Experimental Biology 97®, New Orleans, LA, Apr. 6-9, 1997, An Annual Meeting of Professional Research Scientists, vol. 11, No. 3, Feb. 28, 1997, pp. A447.

(Continued)

*Primary Examiner*—Yvonne Eyler
*Assistant Examiner*—Sudhakar Katakam
(74) *Attorney, Agent, or Firm*—Oblon, Spivak, McClelland, Maier & Neustadt, P.C.

(57) ABSTRACT

The present invention relates a composition having a high content of xanthophyll esters, where the xanthophyll ester component of the composition is comprised of a high proportion of trans-lutein esters. The present invention also provides methods of making and using such a composition.

73 Claims, No Drawings

U.S. PATENT DOCUMENTS

| | | |
|---|---|---|
| 6,787,151 B2 | 9/2004 | Meijer et al. |
| 2003/0130531 A1 | 7/2003 | Sadano et al. |
| 2006/0020030 A1 | 1/2006 | Ornelas-Cravioto et al. |

FOREIGN PATENT DOCUMENTS

| | | |
|---|---|---|
| DE | 1 224 597 | 9/1966 |
| DE | 25 05 869 | 8/1976 |
| EP | 0 672 655 | 9/1995 |
| EP | 1 325 943 | 7/2003 |
| GB | 2 301 775 | 12/1996 |
| JP | 11-322708 | 11/1999 |
| JP | 2000-96032 | 4/2000 |
| WO | WO 93/04598 | 3/1993 |
| WO | WO 95/00130 | 1/1995 |
| WO | WO 95/27483 | 10/1995 |
| WO | WO 96/40092 | 12/1996 |
| WO | WO 97/23436 | 7/1997 |
| WO | WO 98/45241 | 10/1998 |
| WO | WO 99/20587 | 4/1999 |
| WO | WO 99/54408 | 10/1999 |

OTHER PUBLICATIONS

W. Gau, et al., "Mass Spectrometric Identification of Xanthophyll Fatty Acid Esters from Marigold Flowers (Tagetes Erecta) Obtained by High-Performance Liquid Chromatography and Craig Counter-Current Distribution", Journal of Chromatograph, 262 (1983), pp. 277-284.

J.K. Tyczkowski, et al., "Research Note: Preparation of Purified Lutein and Its Diesters from Extracts of Marigold (Tagetes Erecta)[1]", Poultry Science, vol. 70, No. 3, Mar. 1991, pp. 651-654.

D.E. Breithaupt, et al., "Carotenoid Esters in Vegetables and Fruits: A Screening with Emphasis on β-Cryptoxanthin Esters", J. Agric. Food Chem., 2001, 49, pp. 2064-2070.

A. Subagio, et al., "Stability of Lutein and Its Myristate Esters", Biosci. Biotechnol. Biochem., 63 (10), pp. 1784-1786, 1999.

T. Philip, et al., "Utilization of Lutein and Lutein-Fatty Acid Esters by Laying Hens", Journal of Food Science, vol. 41, 1976, pp. 23-25.

Japanese Patent Office, Abstract, JP06-048895, Feb. 22, 1994.

L. Marchand, et al., Int. J. Cancer: 63, 18-23, 1995, "An Ecological Study of Diet and Lung Cancer in the South Pacific".

J. Hachik, et al., J. Agric. Food Chem., 1988, 36, 938-946, "Separation and Identification of Carotenoids and Carotenol Fatty Acid Esters in Some Squash Products by Liguid Chromatograph. 2. Isolation and Characterization of Carotenoids and Related Esters".

H. Kim, et al., Research Communications in Molecular Pathology and Pharmacology, vol. 97, No. 3, Sep. 1997, "Zeaxanthin Dipalmitate from Lycium Chinese Has Heatoprotective Activity".

N. Krinsky, Pur & Appl. Chem., vol. 66, No. 5, 1003-1010, 1994, "The biological Properties of Carotenoids".

J. Landrum, et al., Exp. Eye Res., 1997, 65, 57-62, "A One Year Study of the Macular Pigment: The Effect of 140 Days of a Lutein Supplement".

B. Chew, et al., Anticancer Research, 16, 3689-3694, 1996, "Effects of Lutein from Marigold Extract on Immunity and Growth of Mammary Tumors in Mice".

E. Johnson, et al., American Society for Nutritional Sciences, Human and Clinical Nutrition, pp. 1993-1999, "β-Carotene Isomers in Human Serum, Breast Milk and Buccal Mucosa Cells after Contnuous Oral Doses of All-Trans and 9-Cis β-Carotene[1,2,3]".

J. Landrum, et al., Antioxidants in Disease Mechanisms and Therapy, Advances in Pharmacology, vol. 38, 1997, pp. 537-554, "The Macular Pigment: A Possible Role in Protection from Age-Related Macular Degeneration".

A. Subagio, et al., Biosci. Biotechnol. Biochem., 63 (10), 1784-1786, 1990, "Stability of Lutein and Its Myristate Esters".

W. Hadden, et al., J. Agric. Food Chem., 1999, 47, 4189-4194, "Carotenoid Composition of Marigold (Tagetes erecta) Flower Extract Used as Nutritional Supplement".

D. Breithaup, et al., J. Agric. Food Chem., 2001, 49, 2064-2070, "Carotenoid Esters in Vegetables and Fruits: A Screening with Emphasis on β-Cryptoxanthin Ester".

Important Facts about Xangold, Jun. 2003, published by Cognis, 4 pages.

Park, et al., The FASEB Journal, vol. 11, No. 3, 2556, Feb. 28, 1997, Abstracts 1-3805, Experimental Biology 97, New Orleans, LA, Carotenoids: Investigating The Role in Health and Disease, "The Effect of Dietary Lutein on Growth of Mammary tumor in BALB/c Mice".

The Association for Research Vision and Opthalmology, Investigative Ophthalmology & Visual Science, Feb. 15, 1996, vol. 37, No. 3.

Deutsche Apotheker Zeitung, 1991, 131(3), 72-76, "β-Carotene, Highly Effective on Many cardiac Diseases".

P. Di Mascio, et al., Am J. Clin. Nutr., 1991, 53, 1945-2003, "Antioxidant Defense Systems: The Role of Carotenoids, Tocopherols, and Thiols[1-3]".

N. Krinsky, et al., Free Radical Biology & Medicine, vol. 7, 1989, 617-635, "Antioxidant Functions of Carotenoids".

B. Lim, et al., Biochimica et Biophysica Acta, 1126(1992), 178-184, "Antioxidant Activity of Xanthophylis on Peroxyl Radical-Mediated Phospholipid Peroxidation".

P. Paloza, et al., Methods in Enzymology, vol. 213, Carotenoids (Pt. A), "Antioxidant Effects of Carotenoids in Vivo and in Vitro: An Overview".

M. Chopra, et al., Spec. Publ.-R. Soc. Chem., 1993, 123, Food and Cancer Prevention: Chemical and Biological Aspects, 125-129, "In Vitro Antioxidant Activity of Lutein".

The FASEB Journal, vol. 38, No. 4, Mar. 15, 1997, Investigative Ophthalmology & Visual Science, Abstract Book-Part 1, Annual Meeting Fort Lauderdale, Florida, May 11-16, 1997.

A. Howard, et al., International Journal of Vitamin and Nutrition Research, 1996, 66: 113-118, "Do Hydroxy-Carotenoids Prevent Coronary Heart Disease? A Comparison Between Belfast and Toulouse".

E. Johnson, et al., Journal of Nutrition-Baltimore and Springfield Then Bethesda, 1997, vol. 127, No. 10, 1993-1999, "β-Carotene Isomers in Human Serum, Breast Milk and Buccal Mucosa Cells after Continuous Oral Doses of All-Trans and 9- Cis β-Carotene[1,2,3]".

F. Khachik, et al., J. Agric. Food Chem., 1988, 36, 938-946, "Separation and Identification of Carotenoids and Carotenol Fatty Acid Esters in Some Squash Products by Liquid Chromatography. 2. Isolation and Characterization of Carotenoids and Related Esters".

A. Subagio, et al., Biosci. Biotechnol. Biochem., 63(10), 1784-1786, 1999, "Stability of Lutein and Its Myristate Esters".

J. Terao, Int. Congr. Ser-Excerpta Med., 1994, 329-332, (Frontiers of Reactive Oxygen Species in Biology and Medicine), "Role of Carotenoids in the Antioxidant Defenses on Human Blood Plasma".

J. Tinkler, et al., Journal of Photochemistry and Photobiology, B: Biology 26 (1994), 283-285, "Dietary Carotenoids Protect Human Cells from Damage".

F. Khachik, et al., Journal of Cellular Biochemistry, Supplement 22:236-246, 1995, "Lutein, Lycopene, and Their Oxidative Metabolites in Chemoprevention of Cancer".

H. Nishino, Environ. Mut. Res. Commun., 17:123-126, 1995, "Cancer Chemoprevention by Natural Carotenoids".

M. Mathews-Roth, Pure & Appl. Chem., vol. 57, No. 5, 1985, 717-722, "Carotenoids and Cancer Prevention—Experimental and Epidemiological Studies".

M. Mathews-Roth, Pure & Appl. Chem., vol. 63, No. 1, 1991, 147-156, "Recent Progress in the Medical Applications of Carotenoids".

H. Staeheln, et al., International Journal of Vitamin and Nutrition Research, Beiheft. #30, Elevated Dosages of Vitamins Benefits and Hazards, 232-241, "Preventive Potential of Antioxidative Vitamins and Carotenoids on Cancer".

U.S. Appl. No. 60/042,697, filed on Apr. 4, 1997.

Xantopina Plus, Nutritional Outlook, Jul./Aug. 2000, p. 48, 2 pages; a copy of this document is Exhibit 2 attached to the Declaration of Michael Gibson submitted herewith.

Bioquimex Reka, exact publication date unknown, a copy of this document is Exhibit 3 attached to the Declaration of Michael Gibson submitted herewith; 6 pages.

Facsimile letter dated May 31, 1995 from Chester Sikora to Michael Gibson, Ph.D.; a copy of this document is Exhibit 3 attached to the Declaration of Michael Gibson submitted herewith, 1 page.

Bioquimex Nutrition, Formulating Supplements with Xantopina Plus and Reported Health Benefits and Lutein; exact date of publication unknown, 6 pages.

Bioquimex Nutural, Bioquimex Nutrition, "General Background", 5 pages.

Blue California Press Release, Sep. 28, 2004, published on the World Wide Web, 2 pages.

S. Herbst, et al., The FASEB Journal, vol. 11, No. 3, 2557, Feb. 28, 1997, Abstracts 1-3805, Experimental Biology 97, New Orleans, LA, Carotenoids: Investigating The Role in Health and Disease.

U.S. Appl. No. 11/230,601, filed Sep. 21, 2005, Cravioto.

U.S. Office Action issued Dec. 6, 2006 in corresponding U.S. Appl. No. 11/230,601.

\* cited by examiner

ENHANCED PURITY TRANS-LUTEIN-ESTER COMPOSITIONS AND METHODS OF MAKING SAME

RELATED APPLICATION INFORMATION

This application claims benefit of the filing date of U.S. provisional application Ser. No. 60/589,799, filed on Jul. 22, 2004, and incorporated herein by reference in its entirety.

BACKGROUND OF THE INVENTION

1. Field of the Invention

The present invention relates a composition having a high content of xanthophyll esters, where the xanthophyll ester component of the composition is comprised of a high proportion of trans-lutein esters. The present invention also provides methods of making and using such a composition.

2. Description of the Background

The xanthophylls of marigolds flowers (*Tagetes erecta*) occur acylated with fatty acids (Alam et al., 1968; Phillip and Berry, 1975). These xanthophyll esters belong to a group of natural compounds known as carotenoids and are widely distributed in nature. Xanthophyll esters are mainly fatty acid esters [e.g., palmitate and myristate esters: J. of Food Sci., 51 [4] 1093 (1986)] of carotenoids such as lutein and zeaxanthin. The marigold flower is the richest source of trans-lutein esters found in nature. Dried and ground marigold flowers have been used commercially since 1966 as a coloring agent in animal feed, and, since 1969, they have been used as a starting material for the production of marigold extracts.

Lutein ester is the main xanthophyll pigment, responsible for the yellow/orange color of fruits such as oranges, peaches, papayas, etc. Xanthophyll esters are generally found in nature as trans-xanthophyll isomers.

Recent scientific research has shown that marigold extracts containing lutein esters may be used as nutritional supplements. Among other possible uses in nutrition and medicine, it has been found that lutein esters are specially beneficial in the treatment and prevention of some types of cancer, and in the treatment of a condition known as age-related degeneration of the macula in the human eye (MAD) (see "The effect of Dietary Lutein on growth of mammary tumor BALB/c Mice" The FASEB Journal 11 2586 (1997); International Journal of Cancer 63 18-23 (1995)). It has been reported that consumption of lutein and zeaxanthin reduces the risk of developing MAD up to 40% in mature people (Seddon et al., J. Med. Assoc. 272 [18] 1439-1441 (1994)). Several indicative studies have demonstrated that lutein esters increase the macular pigment density and that the bioavailability is even better than free lutein. (Herbst S, Bowen P, Hussain E, Stacewicz-Sapuntzakis M, Damayanti B, Burns J., Evaluation of the bioavailability of Lutein (L) and Lutein ester (LD) in humans" The FASEB, Journal, 1997; 11:2587 (Abstr.)).

When using lutein esters for human consumption, it is preferable to have the highest possible concentration in the product, and the highest possible trans-lutein content. This is especially important in the nutraceuti cal industry, notably for tableting or elaborating oil formulas.

Several attempts have been made in the past to achieve a high xanthophyll ester concentrate with high trans-lutein content, for example the U.S. Pat. No. 4,048,203 to Phillip describes a process of purification of xanthophyll esters using isopropylic alcohol at 75° C. However this heat treatment results in an undesirably large proportion of the less-bioavailable cis-lutein isomer and a low concentration paste of around 309.25 g/kg (approximately 56% by weight of xanthophyll esters) and a trans-lutein content of 88% by HPLC. Furthermore the resulting paste is sticky and hard to handle.

U.S. Pat. No. 6,191,293 to Levy suggests the treatment of an oleoresin with isopropylic alcohol at 20° C. The resulting product obtained by this procedure has allegedly higher concentration (50% by weight of xanthophyll esters), but with the disadvantage that the marigold petal oleoresin needed for this procedure is not common, and the resulting xanthophyll ester content in the best case is still low (69% by weight of xanthophyll esters).

When using a normal oleoresin derived from whole flowers, instead of petals, and performing the method suggested by U.S. Pat. No. 6,191,293, the resulting paste contained 234 g/kg (approximately 42% by weight of xanthophyll esters) and a trans-lutein content of 84.61%, by HPLC.

U.S. Pat. No. 6,737,535 to Kumar, suggests the use of 2-propanone to obtain a xanthophyll ester concentrate. This procedure results in a product with a concentration of 279 g/kg (approximately 51% by weight of xanthophyll esters) and a profile of 93.4% of trans-lutein, by HPLC.

Even though the profile in this concentrate is better than U.S. Pat. No. 6,191,293, the concentration in this product is still low (<80% by weight of xanthophyll esters) compared to the present invention (>80% by weight of xanthophyll esters as described below).

In view of the foregoing, it is evident that a much better product can be obtained with higher concentration and better chromatographic profile, i.e., a higher proportion of trans-lutein esters.

SUMMARY OF THE INVENTION

It is an object to provide a composition having a high content of xanthophyll esters, where the xanthophyll ester component of the composition is comprised of a high proportion of trans-lutein esters.

It is another object of the invention to provide a method of making compositions having a high content of xanthophyll esters, where the xanthophyll ester component of the composition is comprised of a high proportion of trans-lutein esters.

It is another object of the invention to provide health food and nutritive compositions containing a high content of xanthophyll esters, where the xanthophyll ester component of the composition is comprised of a high proportion of trans-lutein esters.

It is still another object of the present invention to provide methods which utilize compositions which have a high content of xanthophyll esters, where the xanthophyll ester component of the composition is comprised of a high proportion of trans-lutein esters.

More specifically, it is an object of the present invention to obtain a free flowing dry xanthophyll ester of 450 g/kg (81% by weight of xanthophyll esters) to 560 g/kg (100% by weight of xanthophyll esters), in particular a composition containing 530 g/kg (96% by weight of xanthophyll esters), with a minimum chromatographic profile of 94%-96% trans-lutein ester, with 0.1-1% cis-lutein ester and 3-5% trans-zeaxanthin esters. Such a product has the following advantages: it has a very high concentration, at least 450 g/kg (81% by weight of xanthophyll esters), it has a very purified chromatographic profile, 94-96% of trans-lutein ester, it can be obtained from any marigold flower oleoresin without the need of a marigold petal oleoresin, and it is a totally free-flowing dry product.

Still another object of the present invention is a process of purification of the xanthophyll esters using mainly an aliphatic non-polar solvent such as diethyl ether, petroleum ether, n-pentane, n-hexane, n-heptane, more preferably n-hexane, in specified proportions at a temperature from 5° C. to 30° C., especially 18° C. to 22° C., and more preferably 19° C.

The objects of the present invention, and others, may be accomplished with a composition comprising at least 81% by weight, based on the total weight of the composition, of xanthophyll esters, wherein the xanthophylls esters are comprised of at least 94% of trans-lutein esters.

The objects of the present invention may also be accomplished with a method of producing material enriched in trans-lutein ester content, comprising:
  mixing a crude marigold oleoresin and a non-polar solvent to produce a solid suspended in the solvent;
  removing the solvent from the solid; and
  washing the solid with a non-polar solvent.

The objects of the present invention may also be accomplished with a method of producing material enriched in trans-lutein ester content, comprising:
  mixing a crude marigold oleoresin and a non-polar solvent to produce a solid suspended in the solvent;
  removing the solvent from the solid; and
  washing the solid with an alcohol.

The objects of the present invention may also be accomplished with a food or a dietary supplement, comprising the composition described above.

The objects of the present invention may also be accomplished with a method of making a health food or a dietary supplement, comprising incorporating the composition described above into a health food or a dietary supplement.

The objects of the present invention may also be accomplished with a method of treating an eye disease, comprising administering an effective amount of the composition described above to a subject in need thereof.

The objects of the present invention may also be accomplished with a method of treating cancer, comprising administering an effective amount of the composition described above to a subject in need thereof.

The objects of the present invention may also be accomplished with A method of treating a cardiovascular ailment, comprising administering an effective amount of the composition described above to a subject in need thereof.

DESCRIPTION OF THE PREFERRED EMBODIMENTS

As discussed above, the composition comprising at least 81% by weight, based on the total weight of the composition, of xanthophyll esters. The composition may contain 81% to 100% by weight of the of xanthophyll esters. That range includes all specific values and subranges therebetween, such as 82%, 85%, 88%, 90%, 92%, 95%, 96%, 98% and 99% by weight.

The xanthophyll esters, in turn, are comprised at least 94% of trans-lutein esters. In a preferred embodiment, the xanthophylls esters are comprised of 94 to 96% of trans-lutein esters, 0.1 to 1% of cis-lutein esters and 3 to 5% of zeaxanthin esters. Those ranges includes all specific values and subranges therebetween.

According to the present invention, a trans-xanthophyll ester free flowing dry xanthophyll ester can be obtained from the marigold flower oleoresin. The product obtained has a total xanthophyll ester concentration from 450 g/kg (81% by weight of xanthophyll esters) to 560 g/kg (100% by weight of xanthophyll esters), more preferably a product with 530 g/kg concentration (96% by weight of xanthophyll esters), as determined by the method of analysis described in AOAC Official Manual of Analysis, Carotenes and Xanthophylls in Dried Plant Materials and Mixed Feeds Spectrophotometric Analysis, 970.64, 1990, incorporated herein by reference.

In a particularly preferred embodiment of the present invention, the xanthophyll product obtained by the described method has a chromatographic profile of: 94.0-96.0% trans-lutein ester, 0.1-1.0% cis-lutein ester, and 3-5% zeaxanthin ester, a melting point of 82-83° C., a bulk density of 0.35-0.40 g/cm$^3$, and a rest angle of the product of 33.5 degrees.

Regarding the actual quantification of the xanthophyll esters in a concentrate, it has been accepted as a general rough approximation, a method that assumes that the lutein, determined by a spectrophotometric method multiplied by 2.0, gives a fairly good approximation of the actual total weight percentage of the esters (see U.S. Pat. No. 6,737, 535). In some commercial products (Cognis Xangold Esters) a factor of 1.85-2.0 is used, based on some fatty acid analysis, in an attempt to approximate the actual value, but this approximation is still inaccurate.

The method described above specifying multiplying by 2.0 to approximate the percentage of purity of xanthophyll esters, or the method used in commercial products using a factor of 1.85 to 2.0, works well for xanthophyll ester products which have low concentration values (<80% by weight of xanthophyll esters), but they are not suitable for the present invention, because the novel product described herein has a very high xanthophyll ester concentration (>80% by weight of xanthophyll esters).

In the present invention, the spectrophotometric method for xanthophylls, cited above, will be used to determine the concentration of the xanthophyll esters, and this value will be referred to as the "xanthophyll concentration of an ester". The value obtained by this method, is expressed in g/kg of xanthophylls, and this procedure has been found to be the most accurate and reliable method to evaluate the xanthophyll concentration of a xanthophyll ester.

As an approximate value of the equivalent percentage by weight of the xanthophyll ester, and to better understand the advantage of the present invention against other xanthophyll concentrates, a factor of 1.8097 will be used herein, obtained from the composition data published in J. of Food Sci., 51 [4] 1093 (1986), incorporated herein by reference. This value is considered to be a more accurate value (not the exact one) for fatty acid composition of the xanthophyll esters in marigold flowers, than the factor of 2.0 or 1.875 used in other studies. Using the factor of 2.00 described in U.S. Pat. No. 6,737,535, or the factor of 1.875 used in commercial products, the xanthophyll esterconcentration of the product of the present invention, would surpass 100% purity by far.

The chromatographic profile of the xanthophyll esters of the present invention is obtained by HPLC and expressed as a percentage of the total xanthophyll composition, using the following components:
  HPLC-Agilent 1100
  Detector: Visible detector at 447 nm
  Column: Adsorbosphere HS silica 5 microns 250 mm×4.6 mm (Altech 28937)

Mobile phase: Hexane:Ethyl Acetate:Isopropyl Alcohol (70:30:1.5 v/v)

Flow rate: 1.5 ml/min.

According to the present invention, plant material from marigold flowers containing xanthophyll esters is dehydrated, milled and extracted with an aliphatic hydrocarbon solvent. After extraction, the solvent is removed by evaporation under vacuum to obtain an oleoresin rich in trans:cis xanthophyll esters. This oleoresin is the starting material of the present invention.

As discussed above, the present invention provides method of producing material enriched in trans-lutein ester content, comprising:

mixing a crude marigold oleoresin and a non-polar solvent to produce a solid suspended in the solvent;

removing the solvent from the solid; and washing the solid with a non-polar solvent.

In a preferred embodiment, the present invention also relates to a purification process which involves the purification of the xanthophyll esters with an aliphatic non-polar solvent such as diethyl ether, petroleum ether, n-pentane, n-hexane, n-heptane, more preferably n-hexane, in specified proportions, at a temperature from 5° C. to 30° C., especially 18 to 22° C., and more preferably 19° C., followed by a separation of the precipitated trans-xanthophyll esters by any known physical method such as filtration, centrifugation, decantation or any other process to separate solid-liquid phases, followed by evaporation of the solvent phase and drying of the resulting purified trans-xanthophyll ester product.

In a preferred embodiment, the process of making the product also includes drying the washed solid. Drying the solid can produce a dried and free-flowing product. Drying is preferably accomplished in an oven using a nitrogen stream.

The free flowing dry xanthophyll ester thus obtained is suitable for human consumption and has a very high concentration, high purity, and excellent flowability.

According to this invention, the oleoresin obtained by the above method, is mixed with an aliphatic non-polar solvent, such as diethyl ether, petroleum ether, n-pentane, n-hexane or n-heptane, preferably n-hexane, in a proportion from 1:1 to 1:10, preferably 1:1.25 w/v, at a temperature between 5° C. and 30° C., in particular from 18° C. to 22° C., more preferably 19° C., the mixture is gently agitated in order to homogenize the entire oleoresin and induce the precipitation of the trans-xanthophyll esters. After this, the mixture is allowed to settle and the resulting precipitate is separated by any known physical method for liquid-solid separation, e.g., decanting, centrifugation, filtration. The precipitate may then be washed 4 times with an aliphatic non-polar solvent such as diethyl ether, petroleum ether, n-pentane, n-hexane, n-heptane, preferably n-hexane, in an adequate proportion of: 1:0.5 w/v to 1:8, preferably 1:0.65 w/v at a temperature between 5° C. and 30° C. more preferably 19° C. After this operation, the precipitate is filtered under vacuum to remove the excess of solvent, and transferred to a stove to evaporate completely the residual solvent under a stream of nitrogen.

The amount of time for the washing is not particularly limited. Thus, the oleoresin may be allowed to remain in contact for a period of time from 1 to 30 minutes. Preferred times are 5, 10 or 15 minutes.

The product obtained by this process is an orange free flowing dry xanthophyll ester with high xanthophyll concentration and high trans-lutein ester content with the following description: an orange dry product, made of trans-xanthophyll esters, with a concentration of xanthophylls starting from 450 g/kg (81% by weight of xanthophyll esters) to 560 g/kg (100% by weight of xanthophyll esters), more preferably a product with 530 g/kg concentration (96% by weight of xanthophyll esters), as determined by the method of analysis described above.

In another embodiment of the present invention, the solid obtained by mixing a crude marigold oleoresin and a non-polar solvent can be treated with an alcohol solvent, preferably ethanol. In most instances, the process of contacting the oleoresin with the non-polar solvent is sufficient to obtain a purified product. Nevertheless, sometimes the natural oleoresin contains additional impurities that must be purified through an additional washing with the alcohol (preferably ethanol) after the oleoresin has been treated with the non-polar solvent. In this embodiment, the oleoresin is washed at least one time with a non-polar solvent and the product obtained will typically be 280 g/kg (50% by weight of xanthophylls esters). This material is then washed at least once with the alcohol, preferably four times, to obtain a purified trans xanthophylls ester product of, for example, about 480 g/kg (86% by weight of xanthophylls esters). The specific details of the washing procedure with the alcohol may be the same as the non-polar solvent described above.

The product provided by the present invention is suitable for human consumption and can be used as an additive in edible compositions. The product of the present invention may also be incorporated into compositions which are intended for topical use, i.e., application to the skin. Such a composition may be a food or beverage product. In preferred embodiments, the composition of the present invention can be incorporated into health foods and nutritive supplements. In addition, the trans-lutein esters have been studied, to prevent eye diseases such as cataracts and aging macular degeneration; they also have been studied for the treatment of certain diseases like cancer and cardiovascular ailments. Accordingly, the composition of the present invention can be used to treat such conditions. Humans are the preferred subjects for such treatments. These uses are well-known generally are described in, for example, U.S. Pat. Nos. 6,787,147; 6,787,151; 6,716,451; 6,686,340; and 6,660,297, all incorporated herein by reference.

EXAMPLES

Example 1

200 g of marigold oleoresin with a concentration of 112.22 g/kg was mixed with 250 ml of n-hexane at a temperature of 19° C. in a precipitate vessel of 1000 ml. The mixture was gently stirred until it became a homogenous suspension. The resulting mixture was allowed to settle for 10 minutes, the upper phase was then decanted and the resulting precipitate (i.e., the solid) washed with 125 ml of n-hexane, and the upper phase was decanted again. This washing-decanting operation was repeated 4 times, always using 125 ml of n-hexane each time.

The resulting washed precipitate was placed in a vacuum filter to extract the remaining solvent in the precipitate. The filtered precipitate was then placed in an oven and let dry at 45° C. under nitrogen stream for 3 hours.

The resulting dried product weighed 8.36 g (4.18% w/w) with a trans-xanthophyll ester concentration of 522.98 g/kg (19.48% yield of the starting total xanthophylls), 94.64% by weight of trans-xanthophyll esters and a chromatographic profile of 95.01% of trans-lutein by HPLC.

Example 2

10 kg of marigold oleoresin with a concentration of 114.58 g/kg were mixed with 12.5 l of n-hexane at a temperature of 19° C. The mixture was gently stirred for 5 minutes until a homogenous suspension was obtained. The resulting mixture was filtered through a #80 sieve mesh, the retained precipitate was returned to the kettle and washed with 6.5 l of n-hexane and filtered again through the # 80 sieve mesh. This washing operation was repeated 3 times using 6.5 l of n-hexane each time. After this operation, the resulting precipitate was placed in a vacuum filter to remove the excess of n-hexane, then the precipitate was placed in an oven at 45° C. and let dry for 3 hours under a nitrogen stream.

The resulting dried product weighed 0.249 kg (2.49% w/w) with a trans-xanthophyll ester concentration of 535.0 g/kg (11.63% yield of the starting total xanthophylls), 96.81% by weight of trans-xanthophyll esters, and a chromatographic profile of 94.56% of trans-lutein by HPLC.

Example 3

20 kg of marigold oleoresin with a concentration of 169.49 g/kg was mixed with 30 l of n-hexane at a temperature of 19° C. in a stainless steel vessel, the mix was gently stirred until an homogenous mixture was obtained. The resulting suspension was transferred to a centrifuge and centrifuged at 500 rpm for 10 minutes. The resulting paste was transferred back to the stainless steel vessel and washed with 15 l of ethyl alcohol and centrifuged again. The operation was repeated three additional times always using 15 l of ethyl alcohol for each washing.

The resulting washed paste of trans-xanthophyll esters was placed an oven and let dry for 3 hours at a temperature of 45° C. under a nitrogen stream. The resulting dried product was 1.64 kg (8.21 w/w yield) of an orange free flowing product with a concentration of 529.66 g/kg (25.64% yield of the starting total xanthophylls), 95.85% by weight of trans-xanthophyll esters, and a chromatographic profile of 95.07% of trans-lutein by HPLC.

Example 4

15 kg of marigold oleoresin with a xanthophyll concentration of 122.8 g/kg was placed in a stainless steel kettle with 18.75 l of n-hexane at a temperature of 19° C. The mixture was gently stirred until a homogenous suspension was obtained. The resulting mixture was allowed to settle for 15 minutes; the resulting hexanic upper phase was drained from the precipitate, another 9.4 l of n-hexane were added to the drained precipitate, and the hexanic upper phase was again drained from the precipitate. The washing operation with n-hexane was repeated three additional times, always using the same 9.41 l of n-hexane.

The resulting washed paste was centrifuged for 10 minutes at 500 rpm. The resulting precipitate was dried in an oven for 3 hours at 45° C. under nitrogen stream to obtain 0.8325 kg of a dry orange free flowing product (%5.5 w/w yield) and a concentration of 530 g/kg (23.94% yield of the starting total xanthophylls), 95.91% by weight of trans-xanthophyll esters, with a chromatographic profile of 94.68% of trans-lutein by HPLC.

Example 5

16 kg of marigold oleoresin with a xanthophyll concentration of 120.0 g/kg was placed in a stainless steel kettle with 20.0 l of n-hexane at a temperature of 19° C., the mixture was gently stirred until an homogenous suspension was obtained. The resulting mixture was allowed to settle for 15 minutes, the resulting hexanic upper phase was drained from the precipitate, another 10.4 l of n-hexane were added to the drained precipitate, and the hexanic upper phase was drained again from the precipitate. The washing operation with n-hexane was repeated three additional times, always using the same 10.4 l of n-hexane.

The resulting washed paste was filtered in a vibratory filter and washed with 4 l of n-hexane.

The resulting precipitate was dried in an oven for 2.5 hours at 45° C. under nitrogen stream to obtain 0.75 kg of a dry orange free flowing product (% 4.68 w/w yield) and a concentration of 560.15 g/kg (21.88% yield of the starting total xanthophylls), 101.3% by weight of trans-xanthophyll esters, with a chromatographic profile of 96.19% of trans-lutein by HPLC.

Example 6

15 kg of marigold oleoresin with a xanthophyll concentration of 125.3 g/kg was placed in a stainless steel kettle with 18.75 l of n-hexane at a temperature of 19° C., the mixture was gently stirred until an homogenous suspension was obtained. The resulting mixture was filtered on a #80 sieve mesh, the precipitate was returned to the kettle and washed with 9.75l of n-hexane and filtered again on a #80 sieve mesh. This operation was carried over 3 additional times using always 9.75 l of n-hexane for each washing. The resulting precipitate was dried in an oven for 3 hours at 45° C. under nitrogen stream to obtain 0.78 kg of a dry orange free flowing product (% 5.2 w/w yield) and a concentration of 535 g/kg (22.20% yield of the starting total xanthophylls) 96.8% by weight of trans-xanthophyll ester, with a chromatographic profile of 94.10% of trans-lutein by HPLC.

The invention claimed is:

1. A composition comprising at least 85% by weight, based on the total weight of the composition, of xanthophyll esters, wherein the xanthophylls esters are comprised of at least 94% of trans-lutein esters.

2. The composition of claim 1, wherein the xanthophylls esters are comprised of 94 to 96% of trans-lutein esters, 0.1 to 1% of cis-lutein esters and 3 to 5% of zeaxanthin esters.

3. The composition of claim 1, which comprises at least 90% by weight, based on the total weight of the composition, of the xanthophyll esters.

4. The composition of claim 1, which comprises at least 95% by weight, based on the total weight of the composition, of the xanthophyll esters.

5. The composition of claim 1, which comprises at least 96% by weight, based on the total weight of the composition, of the xanthophyll esters.

6. The composition of claim 1, which comprises at least 98% by weight, based on the total weight of the composition, of the xanthophyll esters.

7. The composition of claim 1, which comprises at least 99% by weight, based on the total weight of the composition, of the xanthophyll esters.

8. The composition of claim 1, which contains 100% by weight, based on the total weight of the composition, of the xanthophyll esters.

9. The composition of claim 1, which is in the form of a solid.

10. The composition of claim 1, wherein the xanthophylls esters are comprised of 95 to 96% of trans-lutein esters.

11. The composition of claim 1, which is dry and free-flowing.

12. The composition of claim 1, which has a melting point of 82 to 830C., a bulk density of 0.35 to 0.40 g/cm3, and a rest angle of 33.5 degrees.

13. The composition of claim 1, wherein the xanthophylls esters are comprised of 94 to 96% of trans-lutein esters, 0.1 to 1% of cis-lutein esters and 3 to 5% of zeaxanthin esters, and wherein the composition is dry and free-flowing, has a melting point of 82 to 83°C., a bulk density of 0.35 to 0.40 g/cm3, and a rest angle of 33.5 degrees.

14. A health food or a dietary supplement comprising the composition of claim 1.

15. A food or beverage product comprising the composition of claim 1.

16. A method of producing the composition of claim 1, comprising:
    mixing a crude marigold oleoresin and a n-hexane to produce a solid suspended in the solvent;
    removing the solvent from the solid; and
    washing the solid with a n-hexane solvent.

17. The method of claim 16, further comprising drying the washed solid.

18. The method of claim 16, wherein the washed solid is dried in an oven under a nitrogen atmosphere.

19. The method of claim 16, wherein the crude marigold oleoresin is obtained by extracting xanthophyll esters from marigold meal.

20. The method of claim 16, wherein the n-hexane comprises at least one of diethyl ether and petroleum ether.

21. The method of claim 16, wherein the crude marigold oleoresin and the n-hexane are mixed at a temperature of 5 to 30° C.

22. The method of claim 16, wherein the crude marigold oleoresin and the n-hexane are mixed at a temperature of 18 to 22° C.

23. The method of claim 16, wherein the crude marigold oleoresin and the n-hexane are mixed at a temperature of 19° C.

24. The method of claim 16, wherein the ratio of the crude marigold oleoresin to the n-hexane is 1:1 to 1:10 w/v.

25. The method of claim 16, wherein the ratio of the crude marigold oleoresin to the n-hexane is 1:1 to 1:1.25 w/v.

26. The method of claim 16, wherein n-hexane mixed with the crude marigold oleoresin is the same as or different from the non-polar solvent used to wash the solid.

27. The method of claim 16, wherein the ratio of the solid to the n-hexane in the washing is 1:0.5 to 1:8 w/v.

28. The method of claim 16, wherein the ratio of the solid to the n-hexane in the washing is 1:0.5 to 1:0.65 w/v.

29. The method of claim 16, wherein the washing is conducted at a temperature of 5 to 30° C.

30. The method of claim 16, wherein the washing is conducted at a temperature of 18 to 22° C.

31. The method of claim 16, wherein the washing is conducted at a temperature of 19° C.

32. The method composition of claim 16, wherein the xanthophylls esters are comprised of 94 to 96% of trans-lutein esters, 0.1 to 1% of cis-lutein esters and 3 to 5% of zeaxanthin esters.

33. The method of claim 16, wherein the composition comprises at least 85% by weight, based on the total weight of the composition, of the xanthophyll esters.

34. The method of claim 16, wherein the composition comprises at least 90% by weight, based on the total weight of the composition, of the xanthophyll esters.

35. The method of claim 16, wherein the composition comprises at least 95% by weight, based on the total weight of the composition, of the xanthophyll esters.

36. The method of claim 16, wherein the composition comprises at least 96% by weight, based on the total weight of the composition, of the xanthophyll esters.

37. The method of claim 16, wherein the composition comprises at least 98% by weight, based on the total weight of the composition, of the xanthophyll esters.

38. The method of claim 16, wherein the composition comprises at least 99% by weight, based on the total weight of the composition, of the xanthophyll esters.

39. The method of claim 16, wherein the composition contains 100% by weight, based on the total weight of the composition, of the xanthophyll esters.

40. The method of claim 16, wherein the composition is in the form of a solid.

41. The method of claim 16, wherein the xanthophylls esters are comprised of 95 to 96% of trans-lutein esters.

42. The method of claim 16, wherein the composition is dry and free-flowing.

43. The method of claim 16, wherein the composition has a melting point of 82 to 83° C., a bulk density of 0.35 to 0.40 g/cm3, and a rest angle of 33.5 degrees.

44. The method of claim 16, wherein the xanthophylls esters are comprised of 94 to 96% of trans-lutein esters, 0.1 to 1% of cis-lutein esters and 3 to 5% of zeaxanthin esters, and wherein the composition is dry and free-flowing, has a melting point of 82 to 83° C., a bulk density of 0.35 to 0.40 glcm3, and a rest angle of 33.5 degrees.

45. A method of producing the composition of claim 1, comprising:
    mixing a crude marigold oleoresin and a n-hexane to produce a solid suspended in the solvent;
    removing the solvent from the solid; and
    washing the solid with an alcohol.

46. The method of claim 45, wherein the alcohol is ethanol.

47. The method of claim 45, further comprising drying the washed solid.

48. The method of claim 47, wherein the washed solid is dried in an oven under a nitrogen atmosphere.

49. The method of claim 45, wherein the crude marigold oleoresin is obtained by extracting xanthophyll esters from marigold meal.

50. The method of claim 45, wherein the n-hexane comprises at least one of diethyl ether and petroleum ether.

51. The method of claim 45, wherein the crude marigold oleoresin and the n-hexane are mixed at a temperature of 5 to 30° C.

52. The method of claim 45, wherein the crude marigold oleoresin and the n-hexane are mixed at a temperature of 18 to 22° C.

53. The method of claim 45, wherein the crude marigold oleoresin and the n-hexane are mixed at a temperature of 19° C.

54. The method of claim 45, wherein the ratio of the crude marigold oleoresin to the n-hexane is 1:1 to 1:10 w/v.

55. The method of claim 45, wherein the ratio of the crude marigold oleoresin to the n-hexane is 1:1 to 1:1.25 w/v.

56. The method of claim 45, wherein the washing is conducted at a temperature of 5 to 30° C.

57. The method of claim 45, wherein the washing is conducted at a temperature of 18 to 22° C.

58. The method of claim 45, wherein the washing is conducted at a temperature of 19° C.

59. The method of claim 45, wherein the xanthophylls esters are comprised of 94 to 96% of trans-lutein esters, 0.1 to 1% of cis-lutein esters and 3 to 5% of zeaxanthin esters.

60. The method of claim 45, wherein the composition comprises at least 85% by weight, based on the total weight of the composition, of the xanthophyll esters.

61. The method of claim 45, wherein the composition comprises at least 90% by weight, based on the total weight of the composition, of the xanthophyll esters.

62. The method of claim 45, wherein the composition comprises at least 95% by weight, based on the total weight of the composition, of the xanthophyll esters.

63. The method of claim 45, wherein the composition comprises at least 96% by weight, based on the total weight of the composition, of the xanthophyll esters.

64. The method of claim 45, wherein the composition comprises at least 98% by weight, based on the total weight of the composition, of the xanthophyll esters.

65. The method of claim 45, wherein the composition comprises at least 99% by weight, based on the total weight of the composition, of the xanthophyll esters.

66. The method of claim 45, wherein the composition contains 100% by weight, based on the total weight of the composition, of the xanthophyll esters.

67. The method of claim 45, wherein the composition is in the form of a solid.

68. The method of claim 45, wherein the xanthophylls esters are comprised of 95 to 96% of trans-lutein esters.

69. The method of claim 45, wherein the composition is dry and free-flowing.

70. The method of claim 45, wherein the composition has a melting point of 82 to 83° C., a bulk density of 0.35 to 0.40 g/cm3, and a rest angle of 33.5 degrees.

71. The method of claim 45, wherein the xanthophylls esters are comprised of 94 to 96% of trans-lutein esters, 0.1 to 1% of cis-lutein esters and 3 to 5% of zeaxanthin esters, and wherein the composition is dry and free-flowing, has a melting point of 82 to 83° C., a bulk density of 0.35 to 0.40 g/cm3, and a rest angle of 33.5 degrees.

72. A method of making a health food or a dietary supplement, comprising incorporating the composition of claim 1 into a health food or a dietary supplement.

73. A method of making a food or beverage product, comprising incorporating the composition of claim 1 into a food or beverage product.

* * * * *